United States Patent
Guzi et al.

(10) Patent No.: US 7,166,602 B2
(45) Date of Patent: *Jan. 23, 2007

(54) PYRAZOLOTRIAZINES AS KINASE INHIBITORS

(75) Inventors: Timothy J. Guzi, Chatham, NJ (US); Kamil Paruch, Garwood, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/335,383

(22) Filed: Jan. 19, 2006

(65) Prior Publication Data

US 2006/0122389 A1 Jun. 8, 2006

Related U.S. Application Data

(62) Division of application No. 11/064,044, filed on Feb. 23, 2005, now Pat. No. 7,038,045.

(60) Provisional application No. 60/547,685, filed on Feb. 25, 2004.

(51) Int. Cl.
- *A61K 31/53* (2006.01)
- *A61P 19/02* (2006.01)
- *C07D 251/72* (2006.01)
- *C07D 487/04* (2006.01)

(52) U.S. Cl. ............... 514/245; 514/241; 544/194; 544/206; 544/207

(58) Field of Classification Search ............ 514/245; 544/194, 206, 207
See application file for complete search history.

(56) References Cited

U.S. PATENT DOCUMENTS 3,846,423 A  11/1974  Kobe et al.

FOREIGN PATENT DOCUMENTS

| FR | 2230366 A | 12/1974 |
|---|---|---|
| WO | WO 99/67247 | 12/1999 |
| WO | WO 02/50079 A | 6/2002 |
| WO | WO 02/096348 A | 12/2002 |

OTHER PUBLICATIONS

Cecil Textbook of Medicine, edited by Bennet, J.C., and Plum F., 20th edition,vol. 1, 1004-1010, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Database-Accession No. 1112029 (BRN) 1988, XP002337892 Abstract & Helv. Chim. Acta., vol. 58. 1975. pp. 761-769.
Database-Accession No. 6197252 (BRN) 1988, XP002337893 Abstract & HETEROCYCLES, vol. 22, No. 2, 1984, pp. 345-351.
King F. D.: "Bioisosteres, Conformational Restriction, and Pro-Drugs . . . " Med. Chem: Principles and Practice, Cambridge, RSC, GB, 1994, pp. 206-209, XP002033086.
International Search Report for PCT/US2005/005614—5pgs.

* cited by examiner

*Primary Examiner*—Venkataraman Balasubramanian
(74) *Attorney, Agent, or Firm*—Palaiyur S. Kalyanaraman

(57) ABSTRACT

In its many embodiments, the present invention provides a novel class of pyrazolo[1,5-a]triazine compounds as inhibitors of kinases such as, for example, cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the kinases using such compounds or pharmaceutical compositions.

4 Claims, No Drawings

PYRAZOLOTRIAZINES AS KINASE INHIBITORS

This application is a divisional of patent application Ser. No. 11/064,044 filed Feb. 23, 2005, now U.S. Pat. No. 7,038,045, which claims priority from U.S. Provisional application Ser. No. 60/547,685 filed Feb. 25, 2004.

FIELD OF THE INVENTION

The present invention relates to pyrazolo[1,5-a]triazine compounds useful as protein kinase inhibitors (such as for example, the inhibitors of the cyclin-dependent kinases, mitogen-activated protein kinase (MAPK/ERK), glycogen synthase kinase 3(GSK3beta), checkpoint kinase-1 ("CHK-1"), checkpoint kinase-2 ("CHK-2"), Aurora kinases, (e.g., Aurora A, B, and C), protein kinase B (e.g., serine/threonine kinases such as AKT1, AKT2 and AKT3), and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. This claims priority from U.S. Provisional application, Ser. No. 60/547,685 filed Feb. 25, 2004.

BACKGROUND OF THE INVENTION

Protein kinase inhibitors include kinases such as, for example, the inhibitors of the cyclin-dependent kinases (CDKs), mitogen activated protein kinase (MAPK/ERK), glycogen synthase kinase 3(GSK3beta), checkpoint kinase-1 ("CHK-1"), checkpoint kinase-2 ("CHK-2"), Aurora kinases, (e.g., Aurora A, B, and C), protein kinase B (e.g., serine/threonine kinase such as AKT1, AKT2 and AKT3), and the like. Protein kinase inhibitors are described, for example, by M. Hale et al in WO02/22610 A1 and by Y. Mettey et al in *J. Med. Chem.*, (2003) 46 222–236. The cyclin-dependent kinases are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23— col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986–2999.

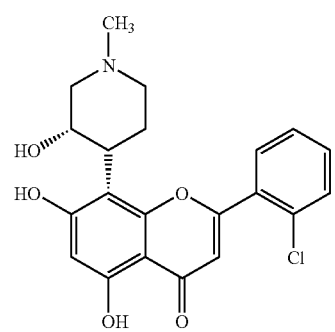

Formula I

Other known inhibitors of the CDKs include, for example, olomoucine (J. Vesely et al, *Eur. J. Biochem.*, (1994) 224, 771–786) and roscovitine (I. Meijer et al, *Eur. J. Biochem.*, (1997) 243, 527–536). U.S. Pat. No. 6,107,305 describes certain pyrazolo[3,4-b]pyridine compounds as CDK inhibitors. An illustrative compound from the '305 patent has the Formula II:

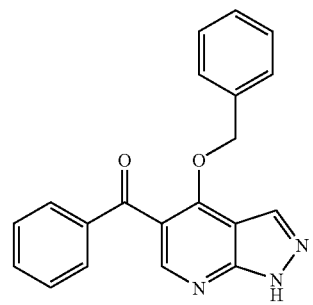

Formula II

K. S. Kim et al, *J. Med. Chem.* 45 (2002) 3905–3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest are: WO 03/101993 (published Dec. 11, 2003), WO 03/091256 (published Nov. 6, 2003), and DE 10223917 (published Dec. 11, 2003). Additionally, pending U.S. patent applications, Ser. Nos. 10/654,546, 10/653,776, 10/654,168, 10/654,163, 10/653,868 and 10/776,988 disclose various pyrazolopyrimidines.

Pyrazolotriazines are known. Some publications disclosing pyrazolotriazines are: WO 99/67247 (published Dec. 29, 1999)DE 2900288 A1, WO 02/096348 (published Dec. 5, 2002), and WO 02/50079 (published Jun. 27, 2002).

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of pyrazolo[1,5-a]triazine compounds as inhibitors of kinases such as for example, cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the kinases, e.g., CDKs, using such compounds or pharmaceutical compositions.

In one aspect, the present application discloses a compound, or pharmaceutically acceptable salts, solvates or esters of said compound, said compound having the general structure shown in Formula III:

Formula III wherein:

$R^1$ is selected from the group consisting of H, alkyl, aryl, heteroaryl, heteroarylalkyl, arylalkyl, $NR^6R^7$, cycloalkyl and cycloalkylalkyl, wherein each of said alkyl, aryl, heteroaryl, heteroarylalkyl, cycloalkyl, cycloalkylalkyl and arylalkyl can be unsubstituted or optionally independently substituted with one or more moieties which can be the same or different, each being independently selected from the group consisting of halo, alkyl, aryl, heteroaryl, heterocyclyl, trifluoromethyl, $OR^6$, $NR^6R^7$, $SR^6$, $SO_2R^6$, CN, $SO_2N(R^6R^7)$ and $NO_2$;

$R^2$ is alkyl, cycloalkyl, alkenyl, alkynyl, trifluoromethyl, $-OR^7$, $-SR^7$, hydroxyalkyl, haloalkyl, aryl, heteroaryl, halo, CN, formyl, nitro, alkylcarbonyl, aralkylcarbonyl, heteroaralkylcarbonyl, or -alkylene-$N(R^8R^9)$ (where $R^8$ and $R^9$ independently represent H or alkyl, or $R^8$ and $R^9$ taken together with the nitrogen in $-N(R^8R^9)$ form a five- to seven-membered heterocycle);

$R^3$ is $-NR^4R^5$,

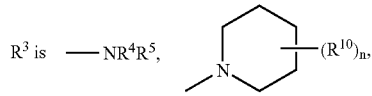

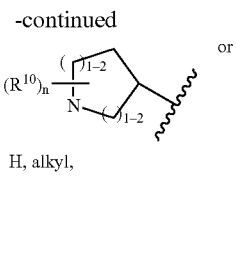

H, alkyl, alkylthio, aralkylthio, alkylsulfinyl, or aralkylsulfinyl;

$R^4$ is alkyl, cycloalkyl or heterocyclyl, wherein each of said alkyl, cycloalkyl and heterocyclyl can be unsubstituted or optionally independently substituted with 1–4 substituents which can be the same or different, each substituent being independently selected from the group consisting of halo, alkyl, hydroxymethyl, hydroxyethyl, hydroxypropyl, trifluoromethyl, $OR^6$, $NR^6R^7$, $SR^6$, $SO_2R^6$, CN, $SO_2N(R6R7)$ and $NO_2$;

$R^5$ is H, alkyl, aryl, heteroaryl, arylalkyl, cycloalkyl, heterocyclyl, acyl or heteroarylalkyl;

$R^6$ is H, alkyl or aryl;

$R^7$ is H or alkyl;

$R^{10}$ is halo, alkyl, hydroxyalkyl, trifluoromethyl, $OR^6$, $NR^6R^7$, $SR^6$, $SO_2R^6$, CN, $SO_2N(R^6R^7)$ or $NO_2$; and n is 0 to 4, and when n is 2–4, the n moieties can be the same or different, each being independently selected, with the following provisos:

(i) that when $R^2$ is $C_1$–$C_4$ alkyl and $R^5$ is H, then $R^4$ is not a $C_1$–$C_4$ alkyl;

(ii) that when $R^2$ is halo, CN, formyl, nitro, alkylcarbonyl, aralkylcarbonyl, heteroaralkylcarbonyl, or -alkylene-N$(R^8R^9)$, then: (a) $R^3$ is not H, alkylthio, aralkylthio, alkylsulfinyl, aralkylsulfinyl, or $-NR^4R^5$, and (b) n is not 0; and (iii) that when $R^2$ is alkyl, cycloalkyl, alkenyl or alkynyl, then $R^3$ is not NH(methyl), N,N(dimethyl), NH(acetyl) or N(methyl)(acetyl).

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]triazine compounds which are represented by structural Formula III, or a pharmaceutically acceptable salt, solvate or ester thereof, wherein the various moieties are as described above.

In another embodiment, $R^1$ is selected from alkyl, aryl, heteroaryl, heteroarylalkyl, arylalkyl or $NR^6R^7$ wherein each of said alkyl, aryl, heteroaryl, heteroarylalkyl and arylalkyl can be unsubstituted or optionally independently substituted with one or more substituents which can be the same or different, each substituent being independently selected from the group consisting of halo, alkyl, aryl, heteroaryl, trifluoromethyl, $OR^6$, $NR^6R^7$, $SR^6$, $SO_2R^6$, CN, $SO_2N(R^6R^7)$ and $NO_2$.

In another embodiment, $R^2$ is alkyl, cycloalkyl, alkynyl, trifluoromethyl, $-OR^7$, or $-SR^7$.

In another embodiment, $R^3$ is $NR^4R^5$,

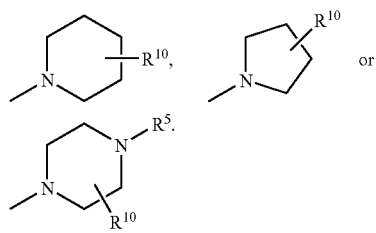

In another embodiment, $R^4$ is alkyl, cycloalkyl or heterocyclyl, wherein each of said alkyl, cycloalkyl or heterocyclyl can be unsubstituted or optionally independently substituted with one or more moieties which can be the same or different, each moiety being independently selected from the group consisting of halo, alkyl, hydroxymethyl, hydroxyethyl, hydroxypropyl, trifluoromethyl, $OR^6$, $NR^6R^7$, $SR^6$, $SO_2R^6$, CN, $SO_2N(R^6R^7)$ and $NO_2$.

In another embodiment, $R^5$ is H, alkyl, aryl, heteroaryl, arylalkyl or heteroarylalkyl.

In another embodiment, n is 1 to 2.

In another embodiment, $R^6$ is H, alkyl or aryl.

In another embodiment, $R^7$ is H or alkyl.

In another embodiment, $R^{10}$ is halo, alkyl, hydroxymethyl, hydroxyethyl, hydroxypropyl, trifluoromethyl, OH, $NR^6R^7$, $SR^6$, $SO_2R^6$, CN or $SO_2NR^6R^7$.

In an additional embodiment, $R^1$ is selected from the group consisting of phenyl, imidazolyl, imidazolyl-N-oxide, pyridyl, pyridyl-N-oxide, pyrazinyl, pyrazinyl-N-oxide, phenethyl, pyridone, $-(CH_2)$-pyridyl, $-(CH_2)$-pyridyl-N-oxide, $-(CH_2)$-pyrazinyl, $-(CH_2)$-pyrazinyl-N-oxide, $-(CH_2)$-pyridone, and $-(CH_2)$-imidazolyl-N-oxide, wherein each of said phenyl, imidazolyl, pyridyl, pyridone, and pyrazinyl can be unsubstituted or optionally independently substituted with one or more moieties which can be the same or different, each moiety being independently selected from the group consisting of halo, methyl, ethyl, trifluoromethyl, OH, alkoxy, $NH_2$, SH, $SO_2CH_3$, CN and $SO_2NH(CH_2)_2CH_3$.

In an additional embodiment, $R^2$ is selected from the group consisting of methyl, ethyl, cyclopropyl, cyclobutyl, cyclopentyl, ethenyl, $-CF_3$, hydroxy, methoxy, and ethoxy.

In an additional embodiment, n is 1.

In an additional embodiment, $R^3$ is selected from the group consisting of:
(i) piperidyl substituted with a hydroxymethyl or hydroxyethyl;
(ii) pyrazinyl substituted with a hydroxymethyl or hydroxyethyl;
(iii) pyrrolidinyl substituted with a hydroxymethyl or hydroxyethyl;
(iv) cyclohexyl substituted with a hydroxymethyl or hydroxyethyl;
(v) cyclopentyl substituted with a hydroxymethyl or hydroxyethyl);
(vi) $-N(H)$(piperidyl substituted with a hydroxymethyl or hydroxyethyl);
(vii $-N(H)$(cyclohexyl substituted with a hydroxymethyl or hydroxyethyl);
(viii) $-N(H)$(cyclopentyl substituted with a hydroxymethyl or hydroxyethyl);
(ix) $-N(H)$(pyrrolidinyl substituted with a hydroxymethyl or hydroxyethyl); and
(x) $-N(H)[CH$ (hydroxymethyl)(isopropyl)].

In an additional embodiment, $R^4$ is alkyl or cycloalkyl.

In an additional embodiment, $R^5$ is H.

In an additional embodiment, $R^6$ is H or alkyl.

In an additional embodiment, $R^7$ is alkyl.

In an additional embodiment, $R^{10}$ is hydroxymethyl or hydroxyethyl.

In a further embodiment, $R^1$ is selected from the group consisting of imidazolyl, imidazolyl-N-oxide, pyridyl, pyridyl-N-oxide, pyrazinyl, pyrazinyl-N-oxide, phenethyl, pyridone, $-(CH_2)$-pyridyl, $-(CH_2)$-pyridyl-N-oxide, $-(CH_2)$-pyrazinyl, $-(CH_2)$-pyridone, and $-(CH_2)$-pyrazinyl-N-oxide;

$R^2$ is selected from the group consisting of methyl, ethyl and cyclopropyl;

n is 1;

$R^3$ is selected from the group consisting of:
(i) piperidyl substituted with a hydroxymethyl or hydroxyethyl;
(ii) pyrazinyl substituted with a hydroxymethyl or hydroxyethyl;
(iii) pyrrolidinyl substituted with a hydroxymethyl or hydroxyethyl;
(iv) cyclohexyl substituted with a hydroxymethyl or hydroxyethyl;
(v) cyclopentyl substituted with a hydroxymethyl or hydroxyethyl);
(vi) $-N(H)$(piperidyl substituted with a hydroxymethyl or hydroxyethyl);
(vii $-N(H)$(cyclohexyl substituted with a hydroxymethyl or hydroxyethyl);
(viii) $-N(H)$(cyclopentyl substituted with a hydroxymethyl or hydroxyethyl);
(ix) $-N(H)$(pyrrolidinyl substituted with a hydroxymethyl or hydroxyethyl); and
(x) $-N(H)[CH$(hydroxymethyl)(isopropyl)];

$R^4$ is alkyl or cycloalkyl;

$R^5$ is H;

$R^6$ is H or alkyl; and $R^7$ is alkyl.

Yet another embodiment discloses the inventive compounds shown in Table 1.

TABLE 1
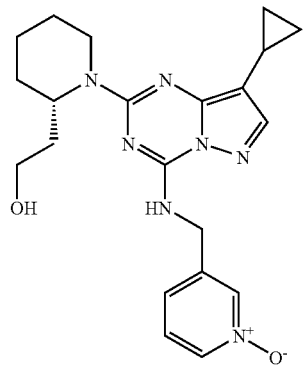 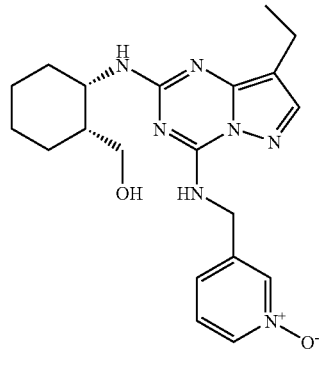 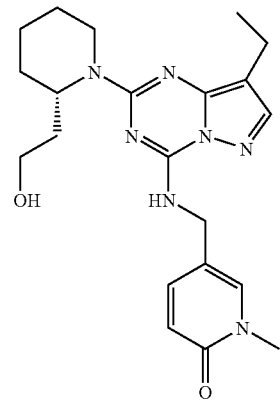
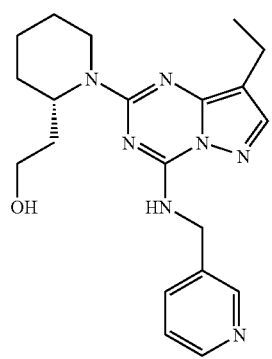 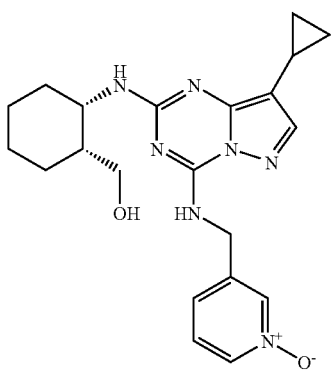 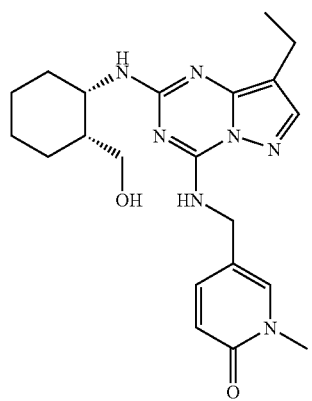
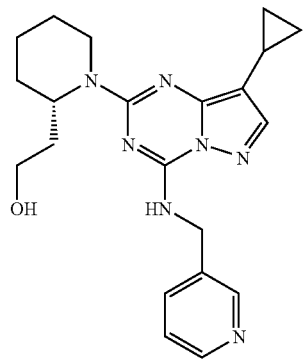 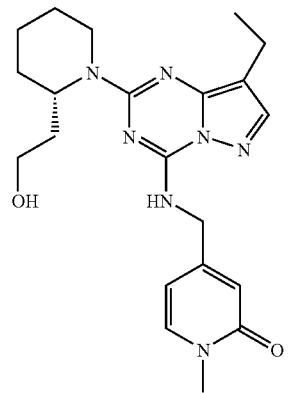 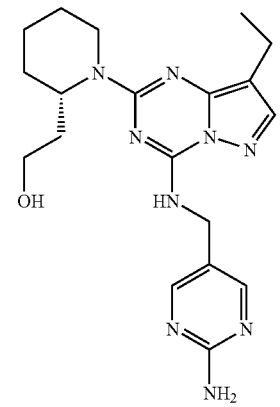
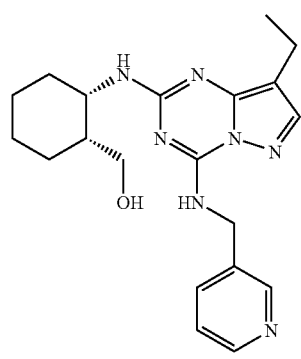 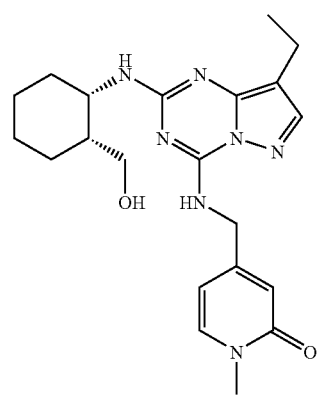 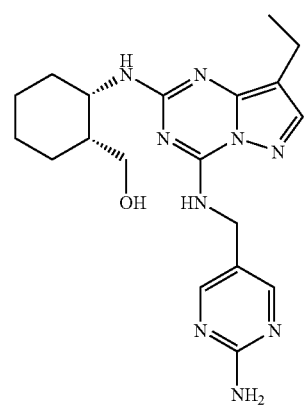

TABLE 1-continued
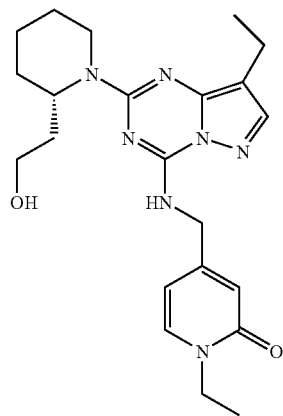 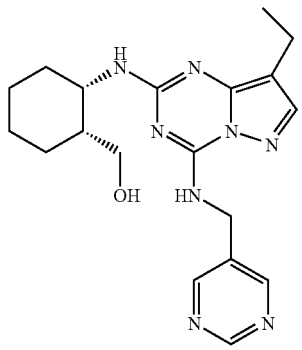 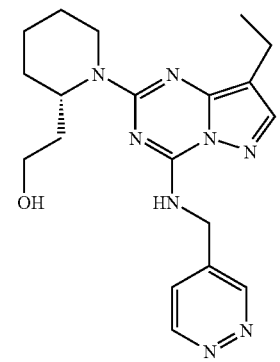
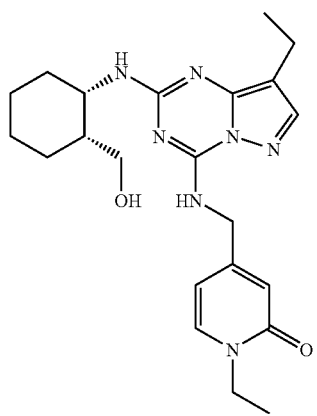 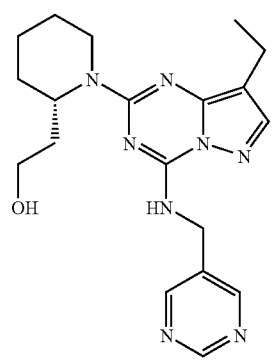 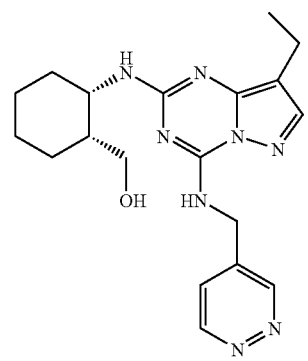
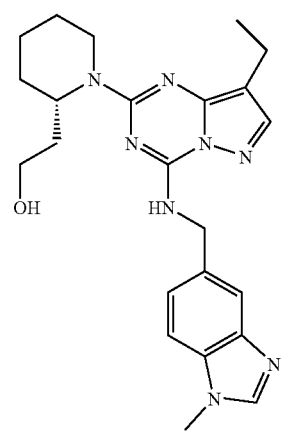 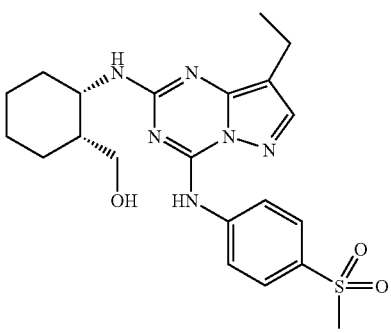 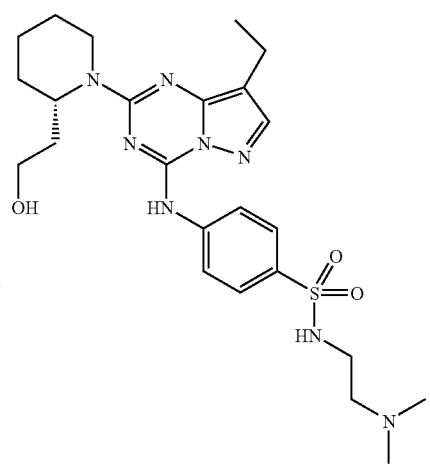

TABLE 1-continued
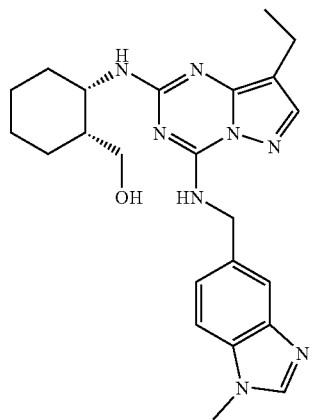 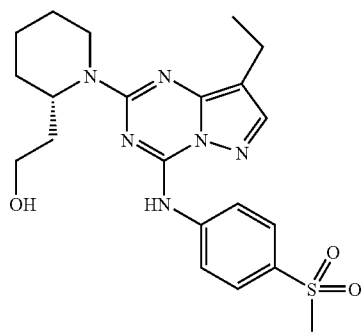 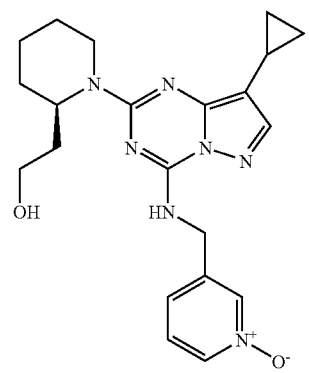
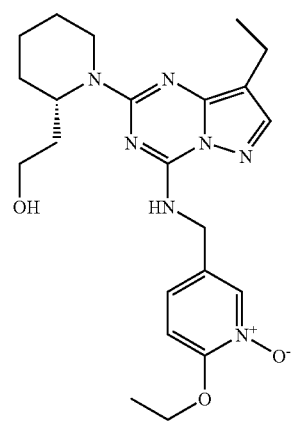 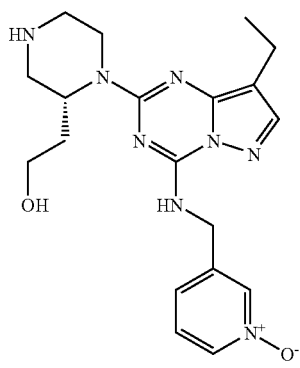 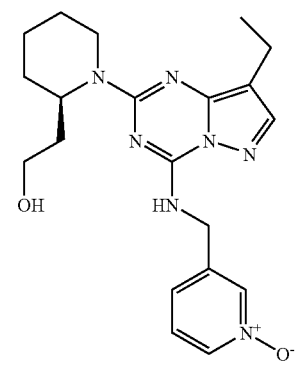
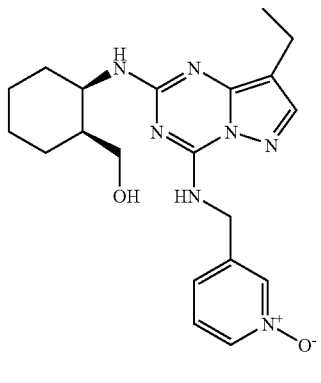 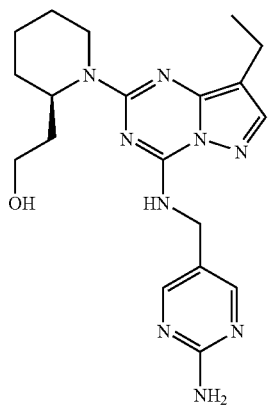 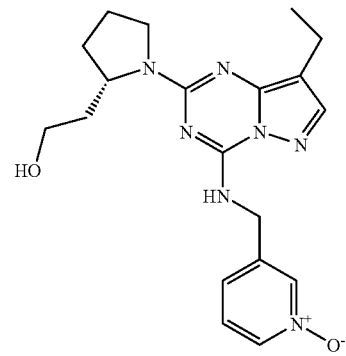
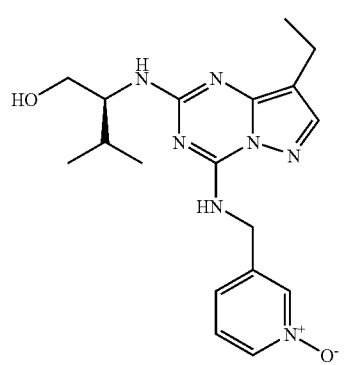 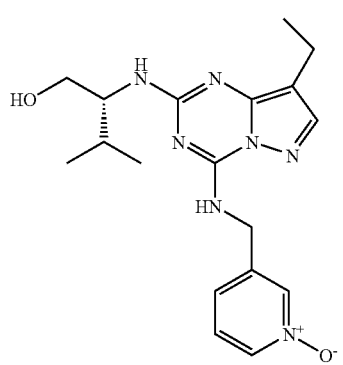 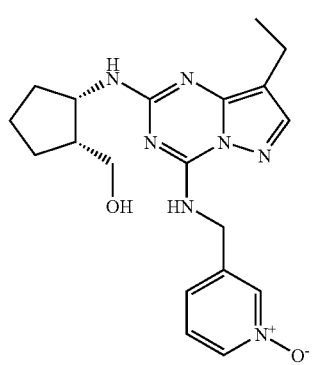

TABLE 1-continued

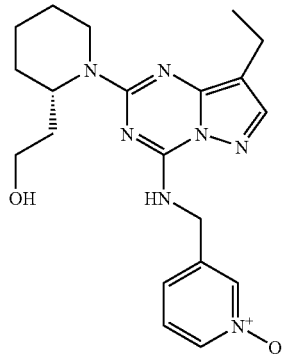

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

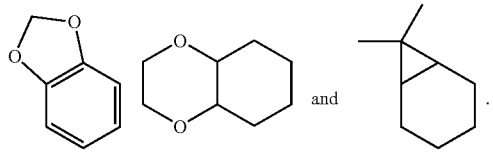

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

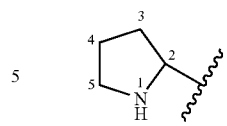

there is no —OH attached directly to carbons marked 2 and 5.

It should also be noted that tautomeric forms such as, for example, the moieties:

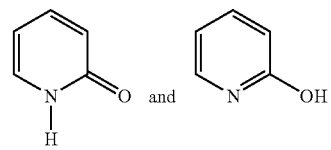

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio.

The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York When any variable (e.g., aryl, heterocycle, $R^2$, etc.) occurs more than one time in any constituent or in Formula III, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III may be formed, for example, by reacting a compound of Formula III with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange*

Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$) acyl glycerol.

Compounds of Formula III, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula III, and of the salts, solvates and prodrugs of the compounds of Formula III, are intended to be included in the present invention.

The compounds according to the invention have pharmacological properties; in particular, the compounds of Formula III can be inhibitors of protein kinases such as, for example, the inhibitors of the cyclin-dependent kinases (e.g., CDK1, CDK2, CDK3, CDK4 CDK5 and the like), mitogen-activated protein kinase (MAPK/ERK), glycogen synthase kinase 3(GSK3beta), checkpoint kinase-1 ("CHK-1"), checkpoint kinase-2 ("CHK-2"), Aurora kinases, (e.g., Aurora A, B, and C), protein kinase B (e.g., serine/threonine kinases such as AKT1, AKT2 and AKT3), and the like. The cyclin dependent kinases (CDKs) include, for example, CDC2 (CDK1), CDK2, CDK4, CDK5, CDK6, CDK7 and CDK8. The novel compounds of Formula III are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula III can be useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula III may also be useful in the treatment of Alzheimer's disease, as suggested by the recent finding that CDK5 is involved in the phosphorylation of tau protein (*J. Biochem*, (1995) 117, 741–749).

Compounds of Formula III may induce or inhibit apoptosis. The apoptotic response is aberrant in a variety of human diseases. Compounds of Formula III, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula III, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III may also be useful in inhibiting tumor angiogenesis and metastasis.

Compounds of Formula III may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III, or a pharmaceutically acceptable salt, solvate or ester of said compound to the mammal.

A preferred dosage is about 0.001 to 500 mg/kg of body weight/day of the compound of Formula III. An especially preferred dosage is about 0.01 to 25 mg/kg of body weight/day of a compound of Formula III, or a pharmaceutically acceptable salt, solvate or ester of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11 -yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III may also be administered sequentially with known anticancer or cytotoxic agents when a combination formulation is inappropriate. The invention is not limited in the sequence of administration; compounds of Formula III may be administered either prior to or after administration of the known anticancer or cytotoxic agent. For example, the cytotoxic activity of the cyclin-dependent kinase inhibitor flavopiridol is affected by the sequence of administration with anticancer agents, *Cancer Research*, (1997) 57, 3375. Such techniques are within the skills of persons skilled in the art as well as attending physicians.

Accordingly, in an aspect, this invention includes combinations comprising an amount of at least one compound of Formula III, or a pharmaceutically acceptable salt, solvate or ester thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later can be carried out with the compounds according to the invention and their salts.

This invention is also directed to pharmaceutical compositions which comprise at least one compound of Formula III, or a pharmaceutically acceptable salt, solvate or ester of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III, or a pharmaceutically acceptable salt, solvate or ester of said compound and a pharmaceutically acceptable carrier, vehicle or diluent.

Yet another aspect of this invention is a kit comprising an amount of at least one compound of Formula III, or a pharmaceutically acceptable salt, solvate or ester of said compound and an amount of at least one anticancer therapy and/or anti-cancer agent listed above, wherein the amounts of the two or more ingredients result in desired therapeutic effect.

The invention disclosed herein is exemplified by the following preparations, proposed pathways and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop, and the retention time and observed parent ion are given.

The following solvents and reagents may be referred to by their abbreviations:

Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL -continued millimoles: mmol
microliters: μl
grams: g
milligrams: mg
room temperature or rt (ambient): about 25° C.
dimethoxyethane: DME

EXAMPLES

In general the compounds described in this invention can be prepared as illustrated in Scheme 1. Acylation of the appropriately substituted 3-aminopyrazole 1 and base-catalyzed cyclization leads to thiol 2.

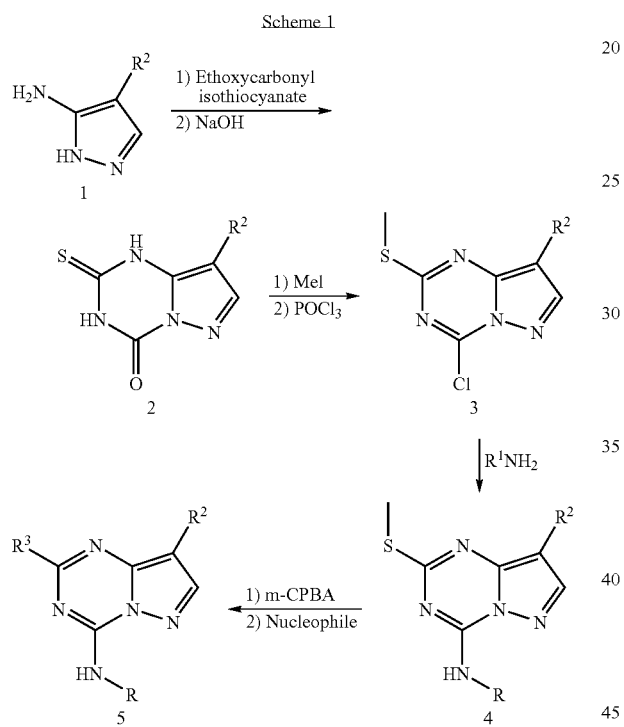

Methylation, chlorination, and displacement with the desired amine gives 4, which can be transformed into the desired products 5 by oxidation and nucleophilic displacement.

Preparative Example 100

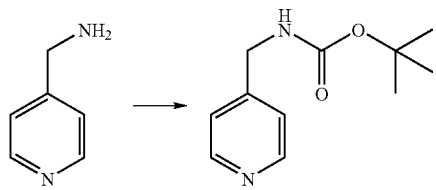

To a solution of 4-aminomethylpyridine (1.41 mL, 13.87 mmol) in $CH_2Cl_2$ (50 mL) was added $BOC_2O$ (3.3 g, 1.1 eq.) and TEA and the resulting solution was stirred a room temperature 2 hours. The reaction mixture was diluted with $H_2O$ (50 mL) and extracted with $CH_2Cl_2$. The combined organics were dried over $Na_2SO_4$, filtered and concentrated under reduced pressure. The crude product was purified by flash chromatography using a 5% (10% $NH_4OH$ in MeOH) solution in $CH_2Cl_2$ as eluent to give a yellow solid (2.62 g, 91% yield). LCMS: $MH^+$=209.

Preparative Example 101

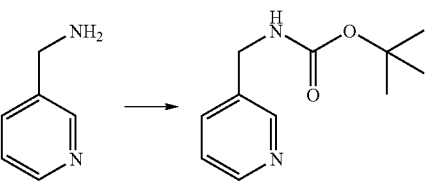

By essentially the same procedure set forth in Preparative Example 100 only substituting 3-aminomethylpyridine, the above compound was prepared as a yellow oil (2.66 g, 92% yield). LCMS: $MH^+$=209.

Preparative Example 200

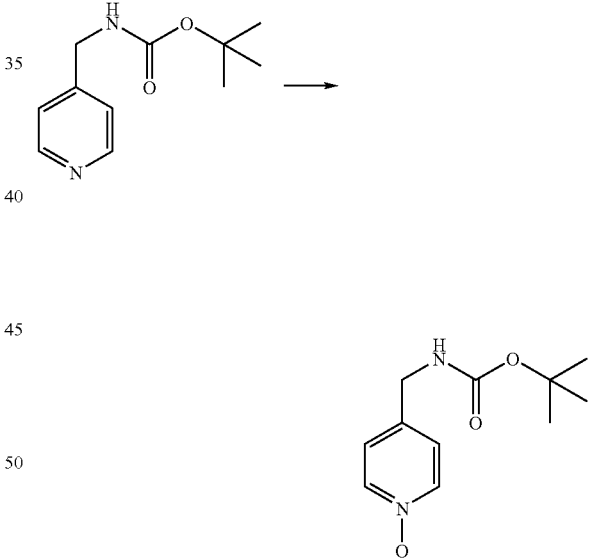

To a solution of the compound prepared in Preparative Example 100 (0.20 g, 0.96 mmol) in $CH_2Cl_2$ (5 mL) at 0° C. was added m-CPBA (0.17 g, 1.0 eq) and the resulting solution stirred at 0° C. 2 hours and stored at 4° C. overnight at which time the reaction mixture was warmed to room temperature and stirred 3 hours. The reaction mixture was diluted with $H_2O$ and extracted with $CH_2Cl_2$. The combined organics were dried over $Na_2SO_4$, filtered, and concentrated. The crude product was purified by flash chromatography using a 10% (10% $NH_4OH$ in MeOH) solution as eluent: LCMS: $MH^+$=255.

Preparative Example 201

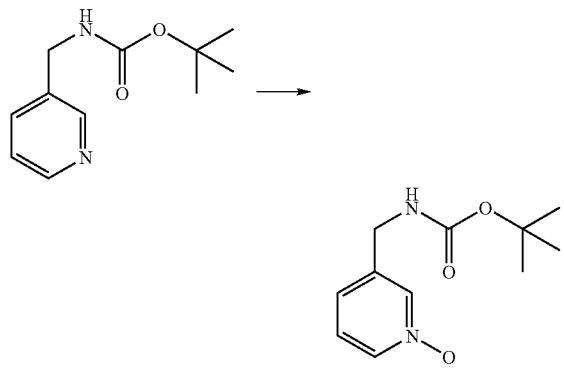

A solution of oxone (58.6 g) in H₂O (250 mL) was added dropwise to the compound prepared in Preparative Example 101 (27 g, 0.13 mol) and NaHCO₃ (21.8 g, 2.0 eq.) in MeOH (200 mL) and H₂O (250 mL). The resulting solution was stirred at room temperature overnight. The reaction mixture was diluted with CH2Cl2 (500 mL) and filtered. The layers were separated and the aqueous layer extracted with CH₂Cl₂. The combined organics were dried over Na₂SO₄, filtered, and concentrated under reduced pressure to give a white solid (21.0 g, 72% yield). MS: MH⁺=255.

Preparative Example 300

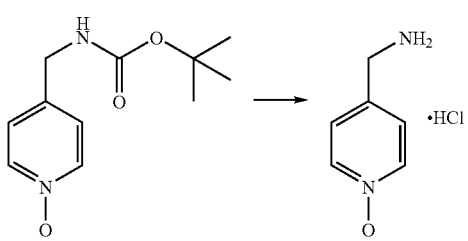

The compound prepared in Preparative Example 200 (0.29 g, 1.29 mmol) was stirred at room temperature in 4M HCl in dioxane (0.97 mL) 2 hours. The reaction mixture was concentrated in vacuo and used without further purification. LCMS: MH⁺=125.

Preparative Example 301

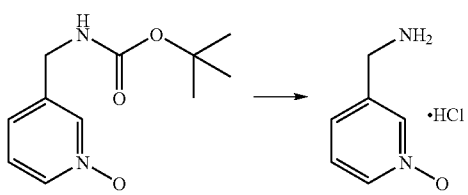

By essentially the same procedure set forth in Preparative Example 201 only substituting the compound prepared in Preparative Example 201, the compound shown above was prepared. LCMS: MH⁺=125.

Preparative Example 400

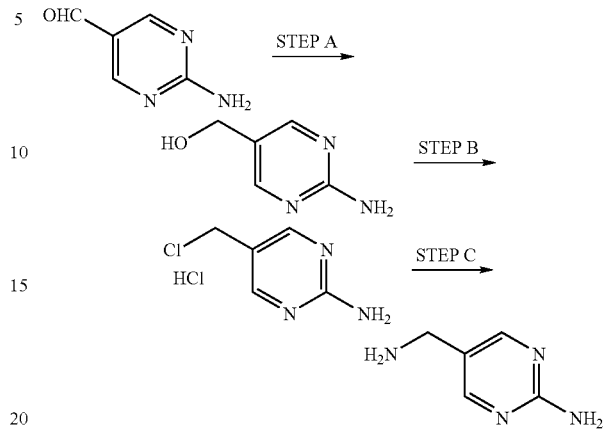

Step A:

A solution of aldehyde (50 g, 0.41 mol) [see, for example, WO 0232893] in MeOH (300 mL) was cooled to 0° C. and carefully treated with NaBH₄ (20 g, 0.53 mol in 6 batches) over 20 minutes. The reaction was then allowed to warm to 20° C. and was stirred for 4 hours. The mixture was again cooled to 0° C., carefully quenched with saturated aqueous NH₄Cl, and concentrated. Flash chromatography (5–10% 7N NH₃—MeOH/CH₂Cl₂) provided the primary alcohol (31 g, 62%) as a light yellow solid.

Step B:

A slurry of alcohol (31 g, 0.25 mol) from Preparative Example 400, Step A in CH₂Cl₂ (500 mL) was cooled to 0° C. and slowly treated with SOCl₂ (55 mL, 0.74 mol over 30 minutes). The reaction was then stirred overnight at 20° C. The material was concentrated, slurried in acetone, and then filtered. The resulting beige solid was dried overnight in vacuo (38.4 g, 52%, HCl salt).

Step C:

To a 15 mL pressure tube charged with a stir bar was added chloride (150 mg, 0.83 mmol) from Preparative Example 400, Step B followed by 7 M NH₃/MeOH (10 mL). The resulting solution was stirred for 48 h at rt whereupon the mixture was concentrated under reduced pressure to afford a light yellow solid (0.146 g, 83%). M+H (free base)=140.

Preparative Example 401

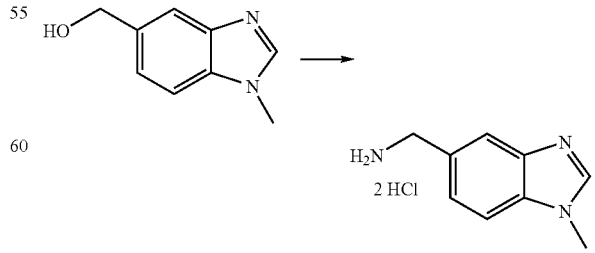

The known primary alcohol was prepared according to WO 00/37473 and was converted to the desired amine dihydrochloride in analogous fashion as Preparative Example 400 according to WO 02/064211.

Preparative Example 500

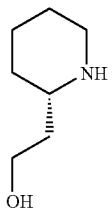

Piperidine-2-ethanol (127 g, 980 mmol) in 95% EtOH (260 mL) was added to (S)-(+)-camphorsulfonic acid (228.7 g, 1.0 eq.) in 95% EtOH (150 mL) and the resulting solution was warmed to reflux. To the warm solution was added Et$_2$O (600 mL) and the solution cooled to room temperature and let stand 3 days. The resulting crystals were filtered and dried in vacuo (25 g): mp 173–173° C. (lit. 168° C.). The salt was then dissolved in NaOH (3M, 100 mL) and stirred 2 hours and the resulting solution was extracted with CH$_2$Cl$_2$ (5×100 mL). The combined organics were dried over Na$_2$SO$_4$, filtered, filtered and concentrated under reduced pressure to give (S)-piperidine-2-ethanol (7.8 g) a portion of which was recrystallized from Et$_2$O: mp=69–70° C. (lit. 68–69° C.); $[\alpha]_D$=14.090 (CHCl$_3$, c=0.2).

Preparative Example 501

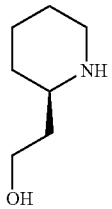

Bye essentially the same procedure set forth in Preparative Example 500 only substituting (R)-(−)-camphorsulfonic acid, (R)-piperidine-2-ethanol was prepared. (1.27 g): $[\alpha]_D$=11.3° (CHCl$_3$, c=0.2).

Preparative Example 502

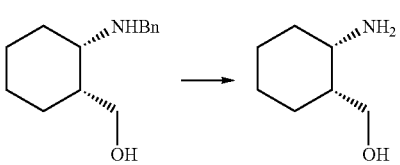

To pressure bottle charged with a solution of cis-(1R,2S)-(+)-2-(Benzylamino)cyclohexanemethanol (1g, 4.57 mmol) in MeOH (35 mL) was added 20% wt Pd(OH)$_2$ (0.3 g, >50% wet) in one portion. The mixture was shaken under 50 psi of H$_2$ in a Parr hydrogenation apparatus for 12 h. The mixture was purged to N$_2$ and was filtered through a pad of Celite. The pad was generously washed with MeOH (2×25 mL) and the resulting filtrate was concentrated under reduces pressure to afford 0.57 g (97%) of a white solid. M+H=130.

Preparative Example 507

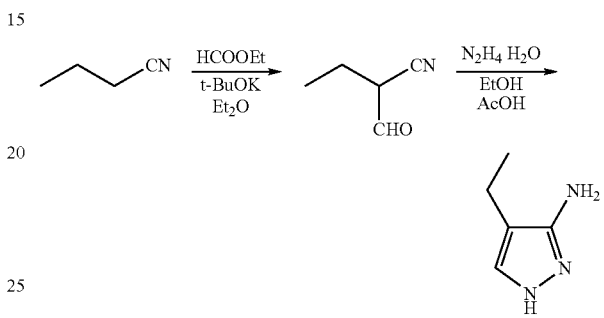

t-BuOK (112.0 g, 1.00 mol) was stirred under N$_2$ in dry Et$_2$O (3.0 L) in a 5 L flask equipped with an addition funnel. A mixture of butyronitrile (69.0 g, 1.00 mol) and ethylformate (77.7 g, 1.05 mol) was added dropwise during 3 hrs, the reaction mixture was then stirred overnight at room temperature. The mixture was cooled to 0° C., AcOH (57 mL) was added, the mixture was filtered, and the solid was washed with Et$_2$O (500 mL). The combined filtrates were evaporated at room temperature on a rotovap to give pale yellow oil (95.1 g).

The oil was dissolved in dry EtOH (100 mL), 99% hydrazine monohydrate (48 mL) was added, then AcOH (14 mL) was added, and the mixture was refluxed under N$_2$ overnight. The solvents were evaporated and the resulting oil was chromatographed on silica gel with CH$_2$Cl$_2$:7N NH$_3$ in MeOH. 22.4 g (20%) of 3-amino-4-ethylpyrazole was obtained as clear oil that solidified upon standing.

Preparative Example 508

| Prep. Ex. | Column 2 |
|---|---|
| 508 | 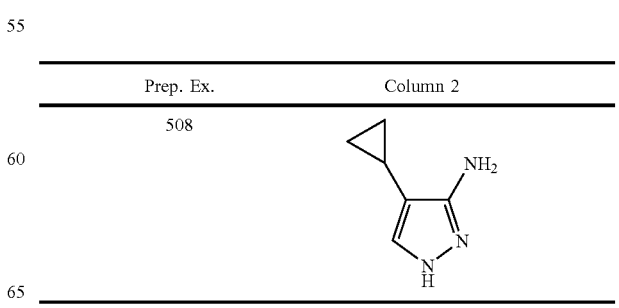 |

By essentially the same procedure set forth in Preparative Example 507 only substituting the appropriate starting materials, the aminopyrazole 508 was prepared.

Preparative Example 509–511

By essentially the same procedure set forth in Preparative Example 507 only substituting the appropriate starting materials, the aminopyrazoles shown in Column 2 of Table 500 are prepared.

TABLE 500

| Prep. Ex. | Column 2 |
| --- | --- |
| 509 | 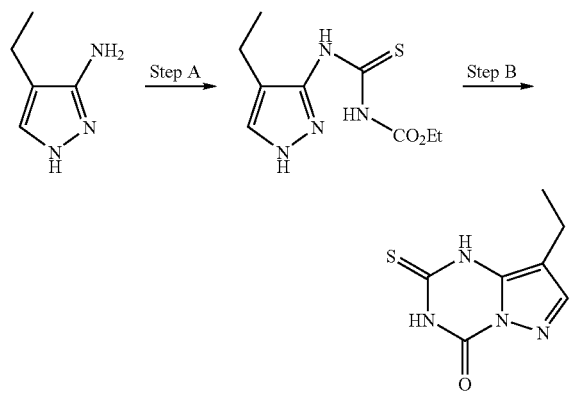 |
| 510 | |
| 511 | |

Preparative Example 512

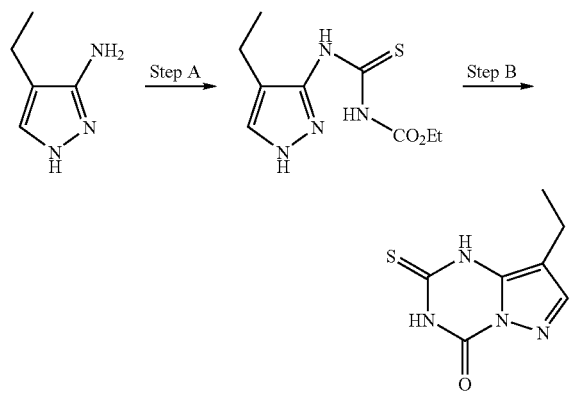

Step A:

To a stirred solution of the pyrazole (3.33 g, 30.0 mmol) from Preparative Example 507 in dry $CH_2Cl_2$ (50 mL) at 0° C. was dropwise added ethoxycarbonyl isothiocyanate (3.54 mL, 3.00 mmol). The resulting mixture was stirred at room temperature 24 hours at which time the precipitate was filtered, washed with $Et_2O$ (2×50 mL), and dried in a vacuum. White solid (3.50 g, 48%) was obtained. LCMS: $MH^+$=243. Mp=177–179° C.

Step B:

A mixture of the solid from Preparative Example 512, Step A (800 mg, 3.30 mmol) and $K_2CO_3$ (1.37 g, 9.90 mmol) in dry acetonitrile (20 mL) was stirred and refluxed under nitrogen for 4 hours. The mixture was cooled to 25° C., acidified with acetic acid (5 mL), and diluted with water (20 mL). The solvents were evaporated and the residue was suspended in water (50 mL). The solid was filtered off, washed on filter with water (2×20 mL), and dried in a vacuum. An off white solid (548 mg, 85%) was obtained. LCMS: $MH^+$=197. Mp=251–253° C.

Preparative Example 513

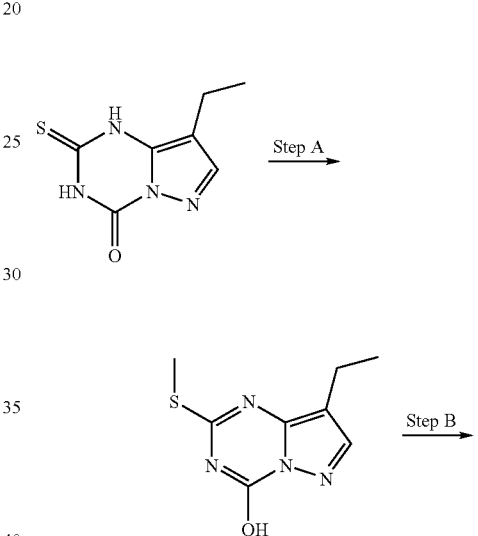

Step A:

To a solution of the compound described in Preparative Example 512 (500 mg, 2.55 mmol) in EtOH was added NaOH (204 mg, 5.10 mmol) in $H_2O$ (3 mL) and then MeI (362 mg, 2.55 mmol) dropwise. The resulting mixture was stirred at room temperature 1 hour, acidified with 1 M HCl (5 mL), and the solvents were evaporated. The residue was purified by column chromatography on silicagel with $CH_2Cl_2$/MeOH (15:1) as eluent to yield a white solid (442 mg, 83%). LCMS: $MH^+$=211. Mp=182–184° C.

Step B:

To a solution of the compound described in Preparative 513, Step A (400 mg, 1.90 mmol) in $POCl_3$ (6 mL) was added N,N-dimethyl aniline (460 mg, 3.80 mmol) and the mixture was heated to reflux under nitrogen for 18 hours.

The resulting solution was poured over crushed ice (200 g) and extracted with $CH_2Cl_2$ (2×50 mL). The combined extracts were washed with $H_2O$ (100 mL), dried over Na2SO4, filtered, and the solvent was evaporated. The residue was purified by column chromatography on silicagel with $CH_2Cl_2$ as eluent to yield a pale yellow solid (275 mg, 63%). LCMS: $M^+$=229.

Preparative Example 514

| Prep. Ex. | Column 2 | Column 3 |
|---|---|---|
| 514 | | |

By essentially the same procedures set forth in Preparative Examples 512–513, compound given in Preparative Example 514 was prepared.

Preparative Example 515–517

By essentially the same procedures set forth in Preparative Examples 512–513, only substituting the compounds shown in Column 2 of Table 501, the compounds shown in Column 3 of Table 501 are prepared.

TABLE 501

| Prep. Ex. | Column 2 | Column 3 |
|---|---|---|
| 515 | | |
| 516 | | |

TABLE 501-continued

| Prep. Ex. | Column 2 | Column 3 |
|---|---|---|

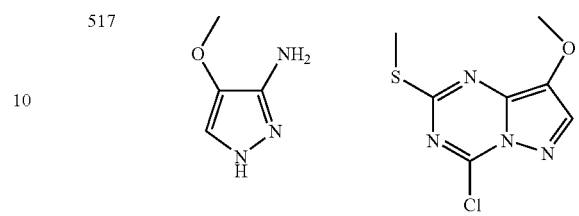

| 517 | | |

Preparative Example 518

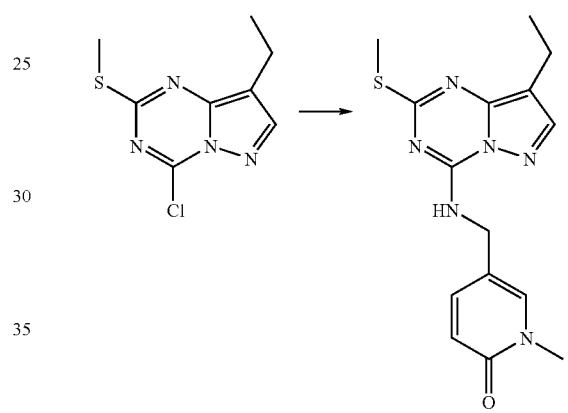

A mixture of the compound from Preparative Example 513 (130 mg, 0.57 mmol), the amine (94 mg, 0.68 mmol), and NaHCO3 (96 mg, 1.14 mmol) in dry acetonitrile (3 mL) was stirred at 70° C. for 20 hours under $N_2$. The solvents were removed under reduced pressure and the residue was purified by column chromatography on silicagel with $CH_2Cl_2$/MeOH (20:1) as eluent to yield a white solid (150 mg, 80%). LCMS: $MH^+$=331. Mp=162–164° C.

Preparative Examples 519–527

By essentially the same procedure set forth in Preparative Example 518 only substituting the amines in Column 3 of Table 502 and the chlorides shown in Column 3 of Table 502, the compounds shown in Column 4 of Table 502 were prepared.

TABLE 502

| Prep. Ex. | Column 2 | Column 3 | Column 4 |
|---|---|---|---|
| 519 | | | |
| 520 | | | |
| 521 | | | |
| 522 | | | |

TABLE 502-continued
| Prep. Ex. | Column 2 | Column 3 | Column 4 |
|---|---|---|---|
| 523 | 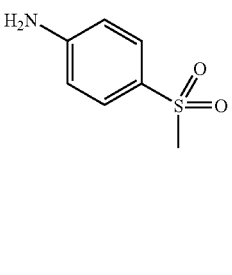 | 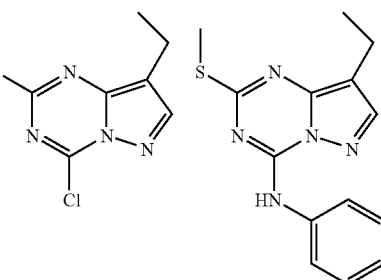 | 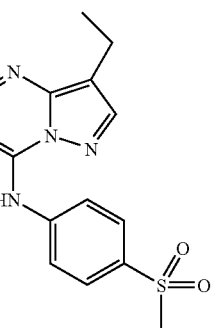 |
| 524 | 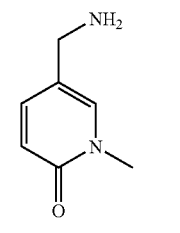 | 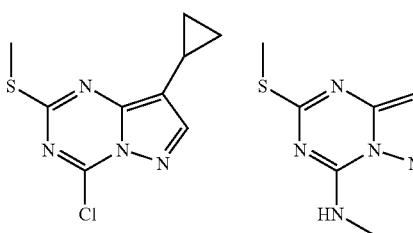 | 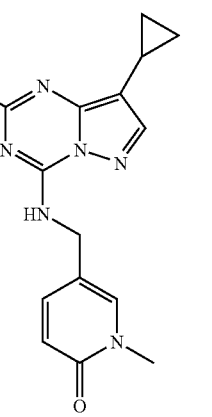 |
| 525 | 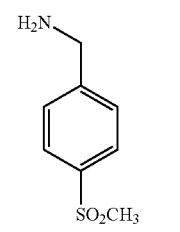 | 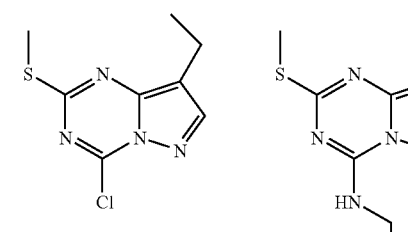 | 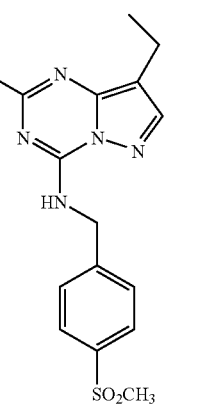 |
| 526 | 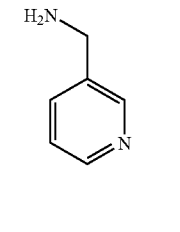 | 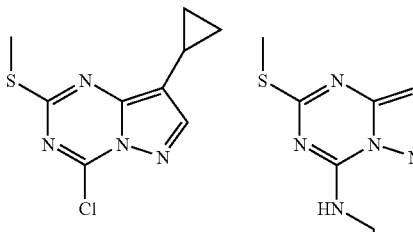 | 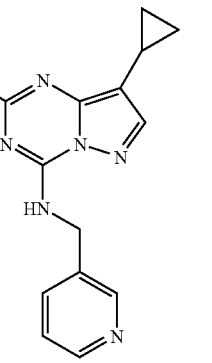 |

TABLE 502-continued

| Prep. Ex. | Column 2 | Column 3 | Column 4 |
|---|---|---|---|
| 527 |  | 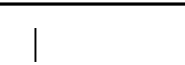 | 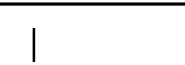 |

Example 1000

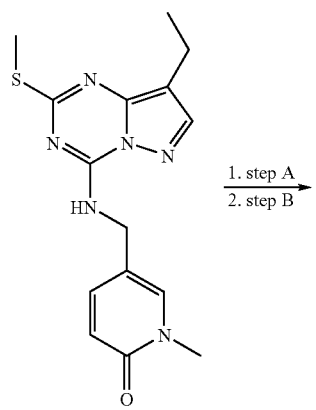

Step A:

To a solution of the compound from Preparative 518 (80 mg, 0.24 mmol) in $CH_2Cl_2$ (5 mL) was added 70% m-CPBA (60 mg, 0.24 mmol). The resulting solution was stirred at room temperature overnight, then additional $CH_2Cl_2$ (15 mL) was added. The solution was washed with aqueous saturated $NaHCO_3$ (2×20 mL), dried over $MgSO_4$, filtered, and the solvent was evaporated. So obtained white solid (55 mg) was used directly for step B.

Step B:

A mixture of the compound from Example 1000, Step A (55 mg) with the aminoalcohol from Preparative Example 500 (60 mg) in dry NMP (0.2 mL) was stirred under $N_2$ at 100° C. for 5 hr. The NMP was removed under reduced pressure and the residue is purified by preparative TLC on silicagel with $CH_2Cl_2$/MeOH (5:1) as eluent to yield a pale yellow waxy (30 mg, 51%). LCMS: $MH^+=412$.

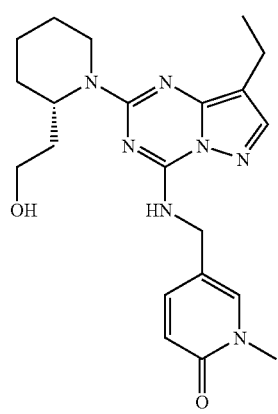

Examples 1001–1010

By essentially the same procedure set forth in Example 1000 only substituting the appropriate amine in Column 2 of Table 1000 and the appropriate thioether in Column 3 of Table 1000 the compounds in column 4 of Table 1000 were prepared.

TABLE 1000

| | | | |
|---|---|---|---|
| 1001 | | | LCMS:<br>MH⁺ = 383.1<br>wax |
| 1002 | | | LCMS:<br>MH⁺ = 398.2<br>mp = 62–67 |
| 1003 | | | LCMS:<br>MH⁺ = 426.2<br>wax |
| 1004 | | | LCMS:<br>MH⁺ = 424.2<br>gummy solid |

TABLE 1000-continued
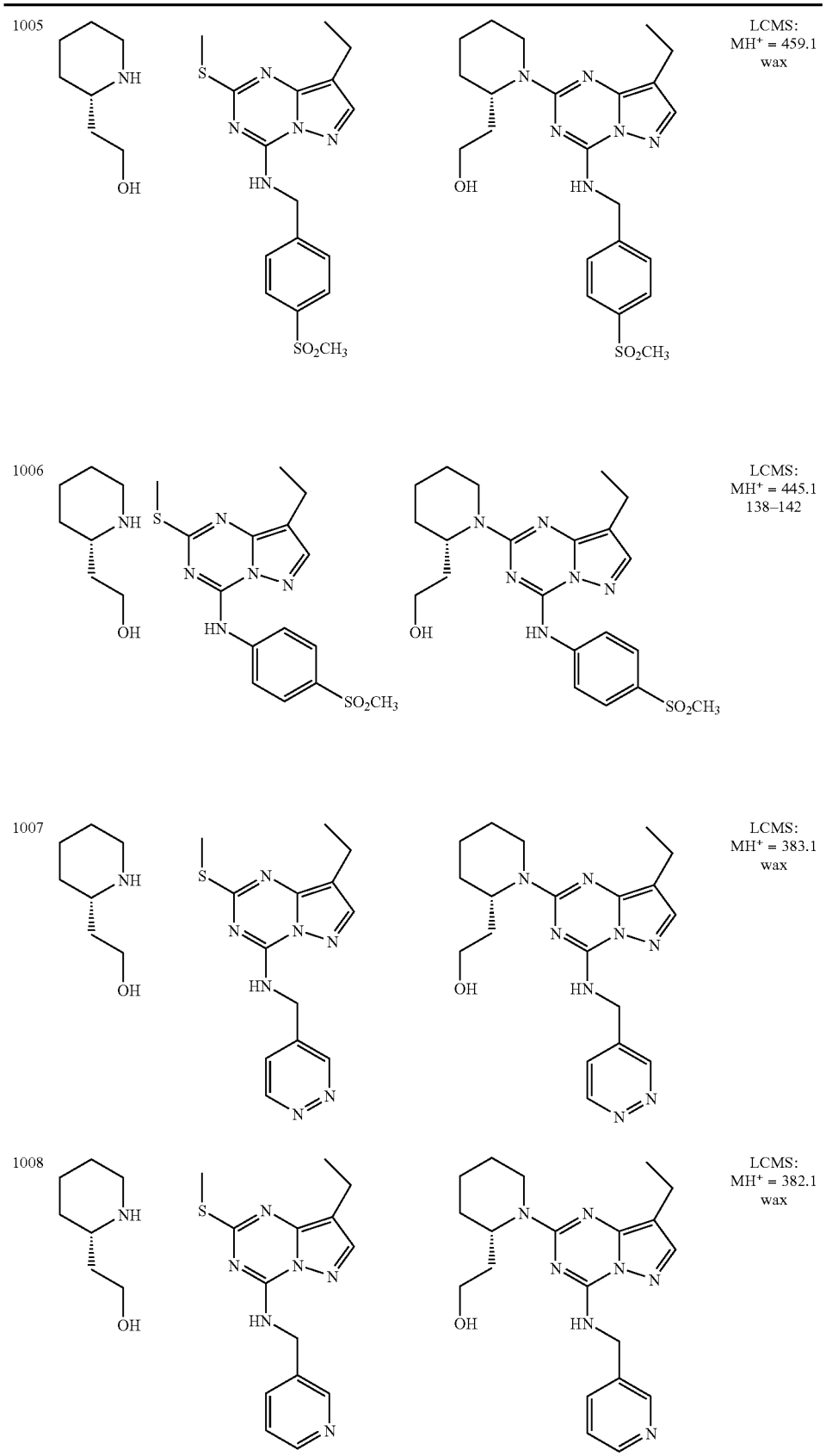
| | | | |
|---|---|---|---|
| 1005 | | | LCMS: MH+ = 459.1 wax |
| 1006 | | | LCMS: MH+ = 445.1 138–142 |
| 1007 | | | LCMS: MH+ = 383.1 wax |
| 1008 | | | LCMS: MH+ = 382.1 wax |

TABLE 1000-continued
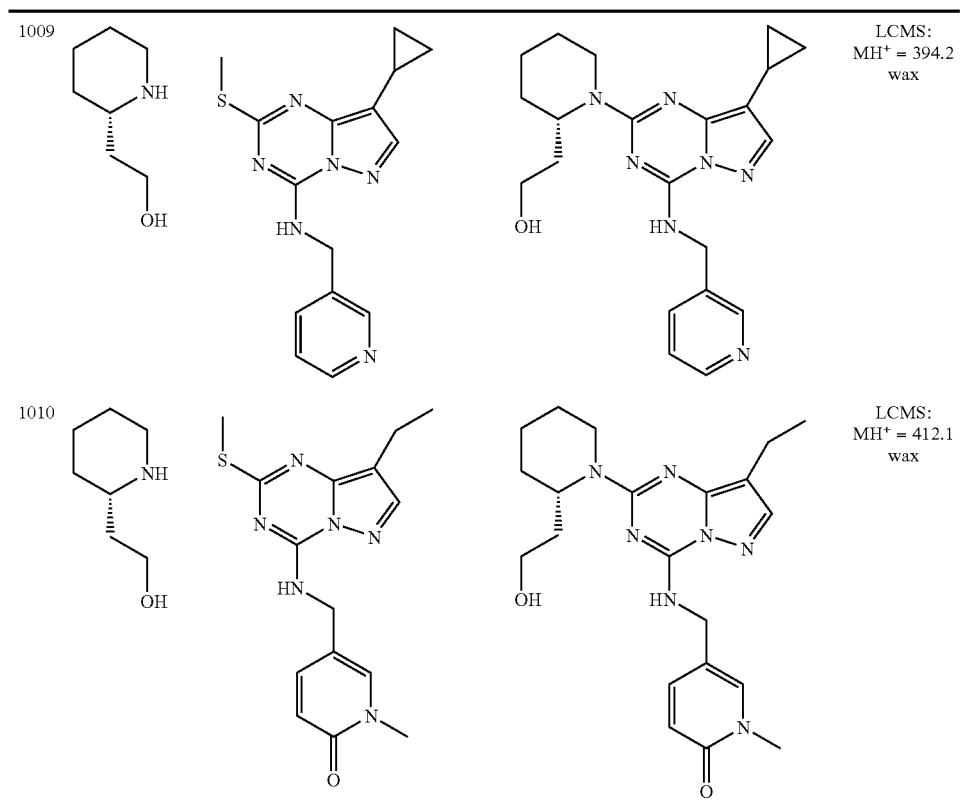
Examples 2001–2029
By essentially the same procedure set forth in Example 1000 only substituting the appropriate amine in Column 2 of Table 2000 and the appropriate thioether in Column 3 of Table 2000 the compounds in column 4 of Table 2000 can be prepared.
TABLE 2000
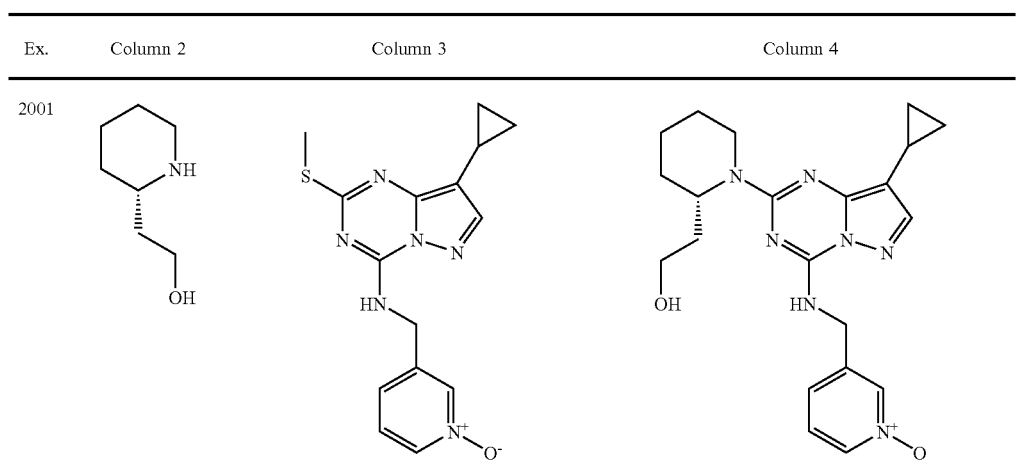

TABLE 2000-continued
| Ex. | Column 2 | Column 3 | Column 4 |
|---|---|---|---|
| 2002 | 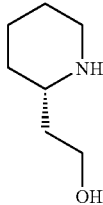 | 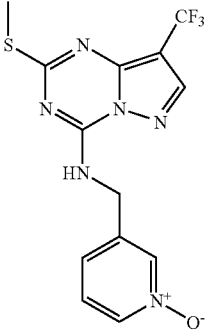 | 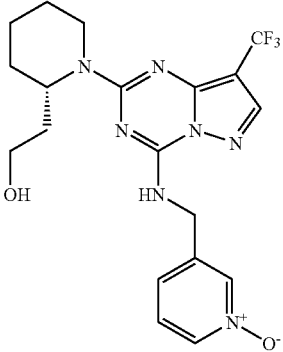 |
| 2003 | 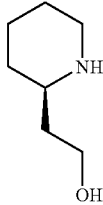 | 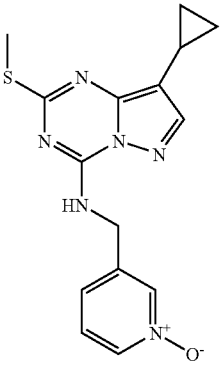 | 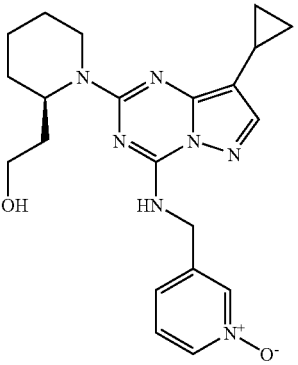 |
| 2004 | 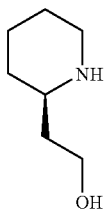 | 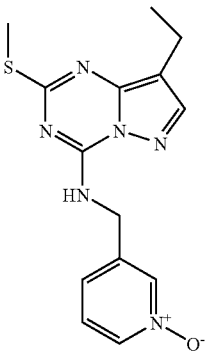 | 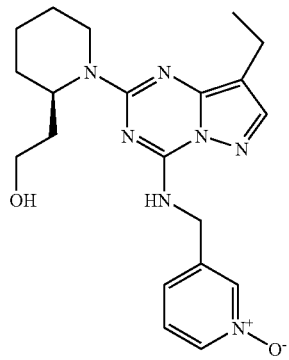 |
| 2005 | 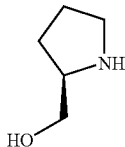 | 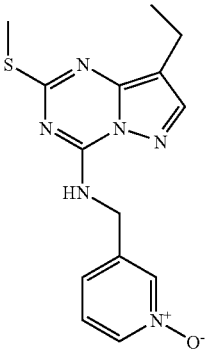 | 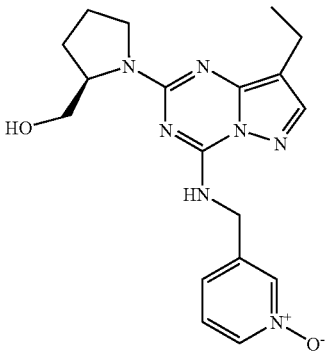 |

TABLE 2000-continued
| Ex. | Column 2 | Column 3 | Column 4 |
|---|---|---|---|
| 2006 | 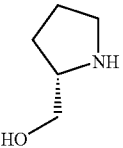 | 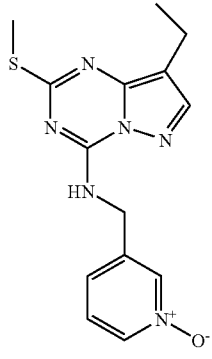 | 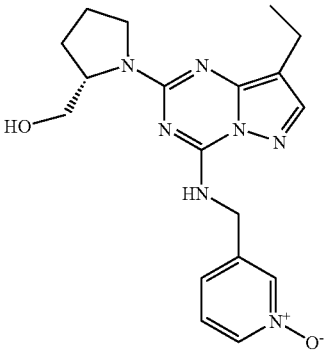 |
| 2007 | 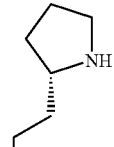 | 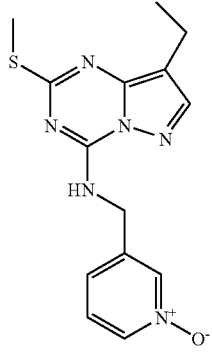 | 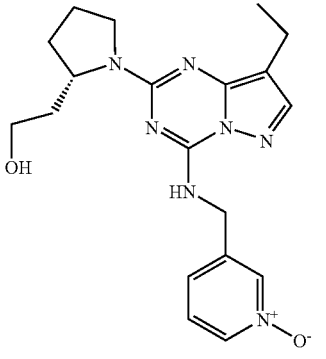 |
| 2008 | 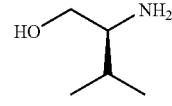 | 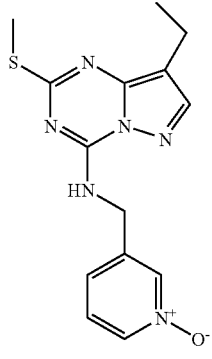 | 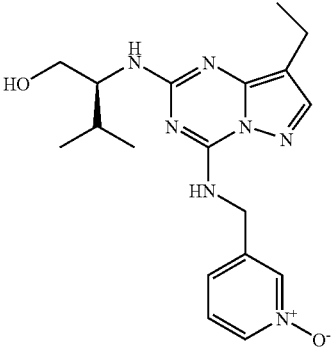 |
| 2009 | 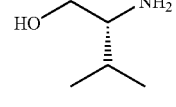 | 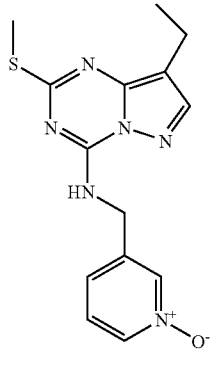 | 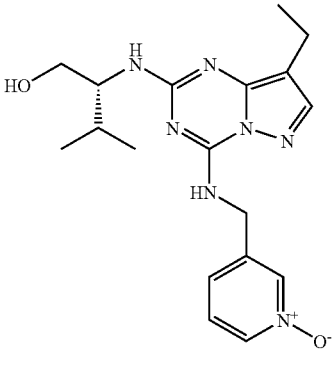 |

TABLE 2000-continued

| Ex. | Column 2 | Column 3 | Column 4 |
|---|---|---|---|
| 2010 | | | |
| 2011 | | | |
| 2012 | | | |
| 2013 | | | |

TABLE 2000-continued
| Ex. | Column 2 | Column 3 | Column 4 |
|---|---|---|---|
| 2014 | 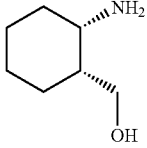 | 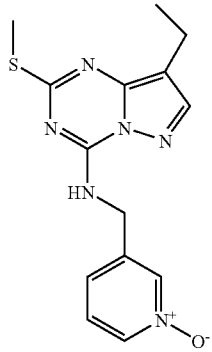 | 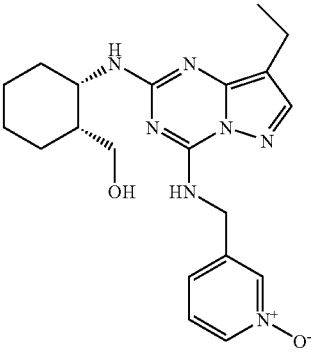 |
| 2015 | 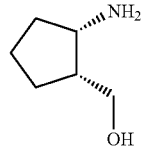 | 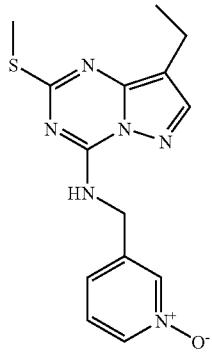 | 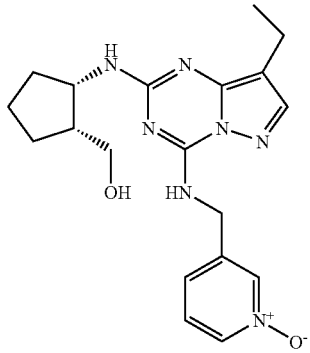 |
| 2016 | 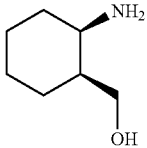 | 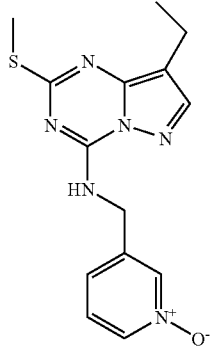 | 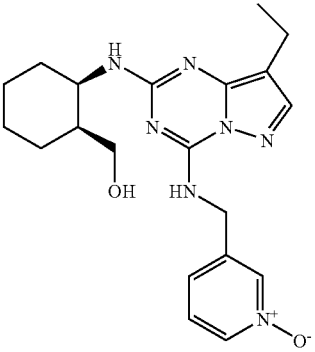 |
| 2017 | 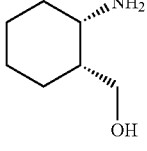 | 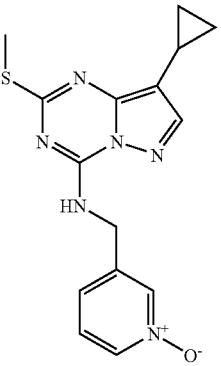 | 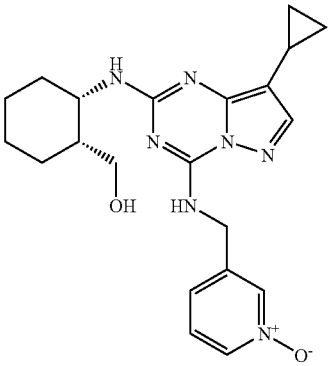 |

US 7,166,602 B2
55                                                                                              56
TABLE 2000-continued
| Ex. | Column 2 | Column 3 | Column 4 |
|---|---|---|---|
| 2018 | 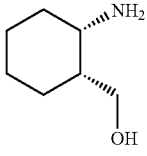 | 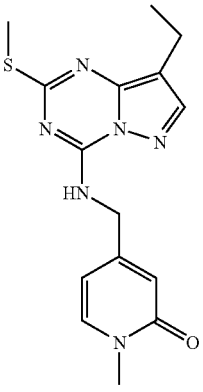 | 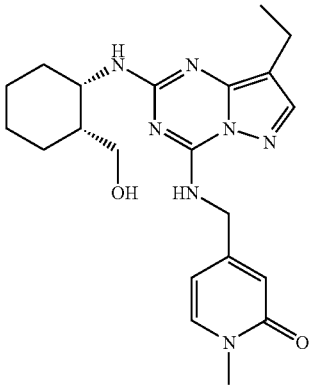 |
| 2019 | 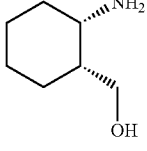 | 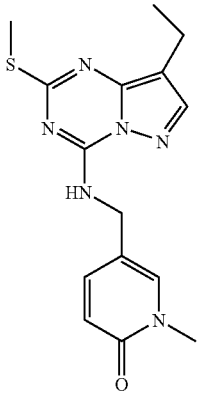 | 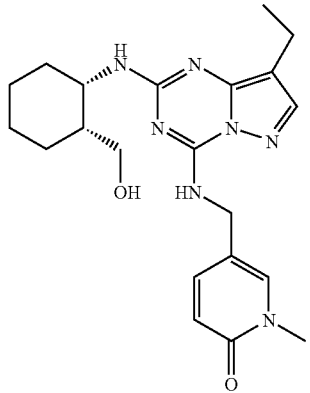 |
| 2020 | 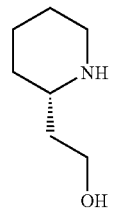 | 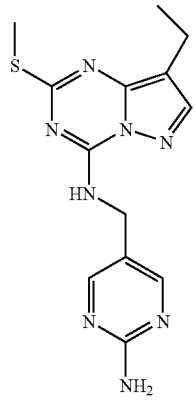 | 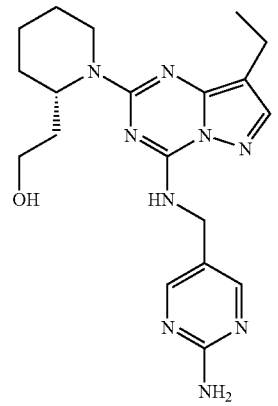 |

TABLE 2000-continued
| Ex. | Column 2 | Column 3 | Column 4 |
|---|---|---|---|
| 2021 | 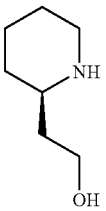 | 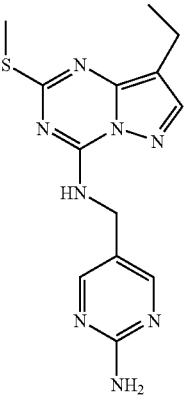 | 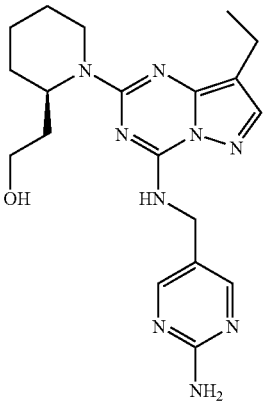 |
| 2022 | 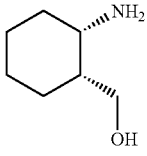 | 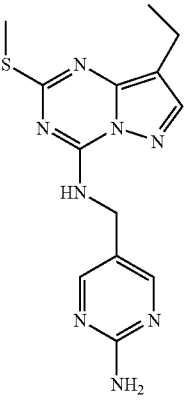 | 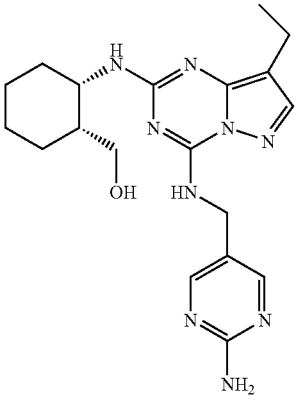 |
| 2023 | 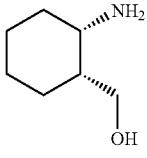 | 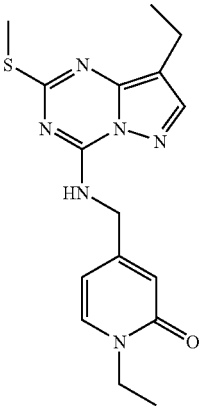 | 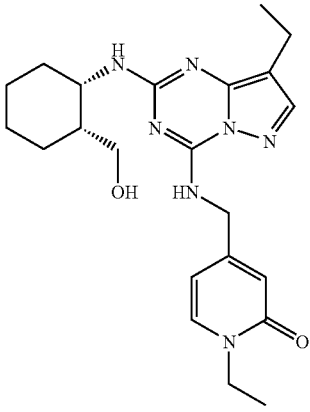 |

TABLE 2000-continued
| Ex. | Column 2 | Column 3 | Column 4 |
|---|---|---|---|
| 2024 | 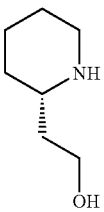 | 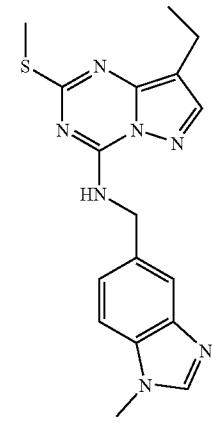 | 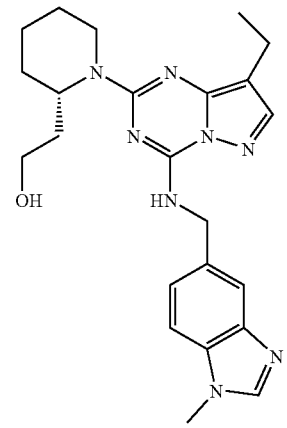 |
| 2025 | 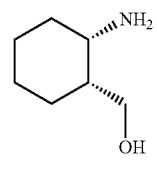 | 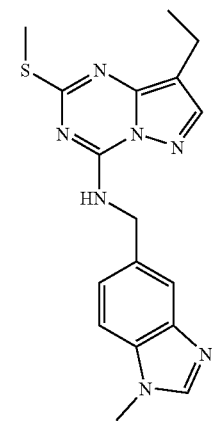 | 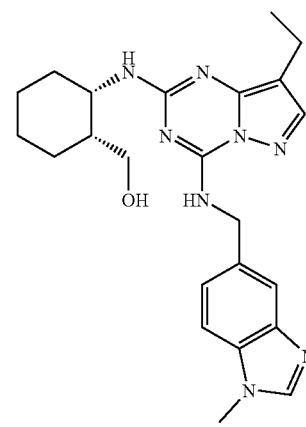 |
| 2026 | 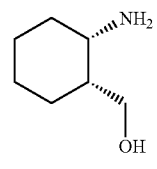 | 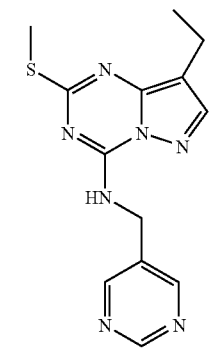 | 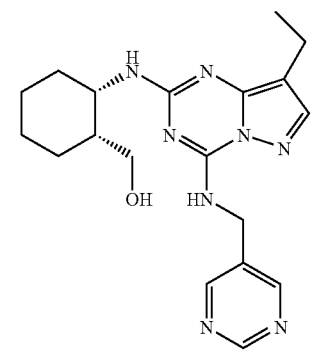 |
| 2027 | 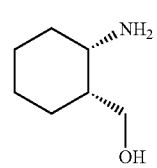 | 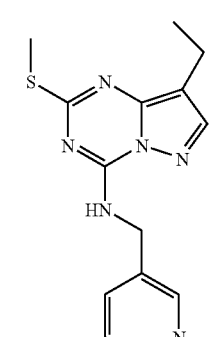 | 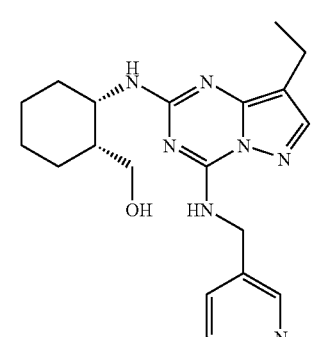 |

TABLE 2000-continued

| Ex. | Column 2 | Column 3 | Column 4 |
|-----|----------|----------|----------|
| 2028 | 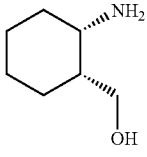 | 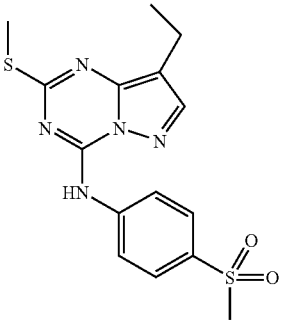 | 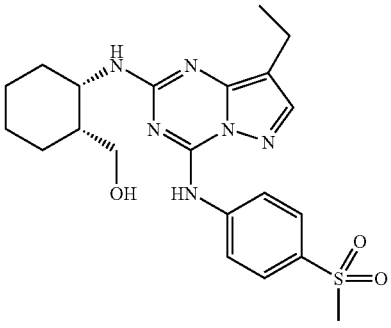 |
| 2029 | 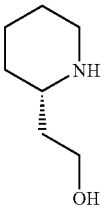 | 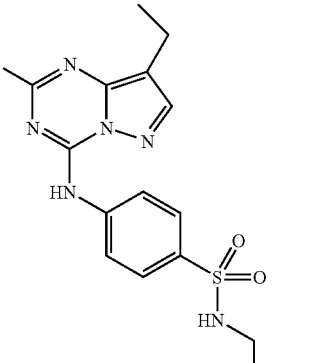 | 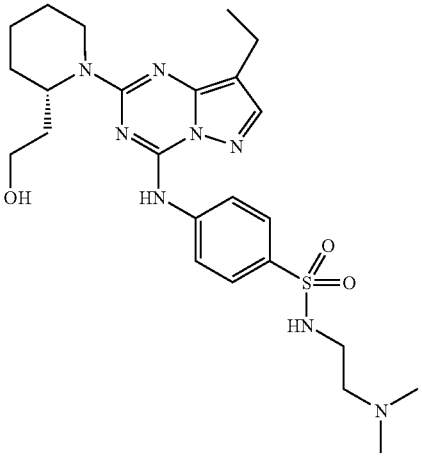 |

Assay

A useful assay for kinase activity is described below.

BACULOVIRUS CONSTRUCTIONS: Cyclins A and E are cloned into pFASTBAC (Invitrogen) by PCR, with the addition of a GluTAG sequence (EYMPME) at the amino-terminal end to allow purification on anti-GluTAG affinity columns. The expressed proteins are approximately 46 kDa (cyclin E) and 50 kDa (cyclin A) in size. CDK2 is also cloned into pFASTBAC by PCR, with the addition of a haemaglutinin epitope tag at the carboxy-terminal end (YD-VPDYAS). The expressed protein is approximately 34 kDa in size.

ENZYME PRODUCTION: Recombinant baculoviruses expressing cyclins A, E and CDK2 are infected into SF9 cells at a multiplicity of infection (MOI) of 5, for 48 hrs. Cells are harvested by centrifugation at 1000 RPM for 10 minutes. Cyclin-containing (E or A) pellets are combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures are stirred for 30–60 minutes to promote cyclin-CDK2 complex formation. Mixed lysates are then spun down at 15000 RPM for 10 minutes and the supernatant retained. 5ml of anti-GluTAG beads (for one liter of SF9 cells) are then used to capture cyclin-CDK2 complexes. Bound beads are washed three times in lysis buffer. Proteins are competitively eluted with lysis buffer containing 100–200 ug/mL of the GluTAG peptide. Eluate is dialyzed overnight in 2 liters of kinase buffer containing 50 mM Tris pH 8.0, 1 mM DTT, 10 mM MgCl2, 100 uM sodium orthovanadate and 20% glycerol. Enzyme is stored in aliquots at −70° C.

IN VITRO KINASE ASSAY: CDK2 kinase assays (either cyclin A or E-dependent) are performed in low protein binding 96-well plates (Corning Inc, Corning, N.Y.). Enzyme is diluted to a final concentration of 50 μg/ml in kinase buffer containing 50 mM Tris pH 8.0, 10 mM $MgCl_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Compounds were diluted in 10% DMSO to desirable concentrations. For each kinase reaction, 20 μl of the 50 μg/ml enzyme solution (1 μg of enzyme) and 20 μl of the 1 μM substrate solution are mixed, then combined with 10 μl of diluted compound in each well for testing. The kinase reaction is started by addition of 50 μl of 4 μM ATP and 1 μCi of 33P-ATP (from Amersham, UK). The reaction is allowed to run for 1 hour at room temperature. The reaction is stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal is then measured using a TopCount 96 well liquid scintillation counter (from Packard/Perkin Elmer Life Sciences).

IC$_{50}$ DETERMINATION: Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate IC$_{50}$ values, the dose-response curves are then fitted to a standard sigmoidal curve and IC$_{50}$ values are derived by nonlinear regression analysis. Kinase activities can be generated by using cyclin A or cyclin E using the above-described assay. The IC$_{50}$ of some of the inventive compounds is shown below in Table 2:

TABLE 2-continued

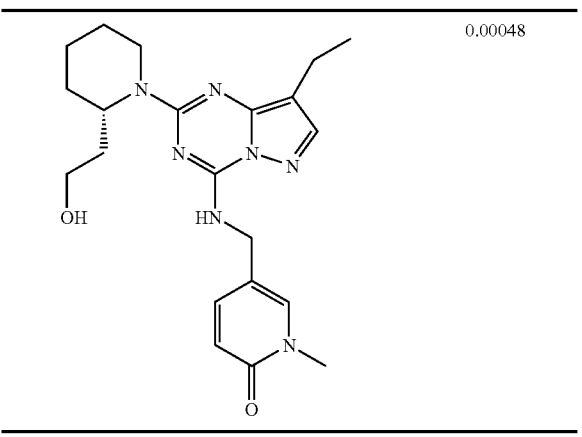

0.00048

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A pharmaceutical composition comprising a therapeutically effective amount of at least one compound of the following formula, or a pharmaceutically acceptable salt, or ester of said compound, in combination with at least one pharmaceutically acceptable carrier;

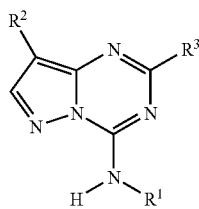

wherein:

$R^1$ is selected from the group consisting of H, alkyl, aryl, heteroaryl, heteroarylalkyl, arylalkyl, $NR^6R^7$, cycloalkyl and cycloalkylalkyl, wherein each of said alkyl, aryl, heteroaryl, heteroarylalkyl, cycloalkyl, cycloalkylalkyl and arylalkyl can be unsubstituted or optionally independently substituted with one or more moieties which can be the same or different, each being independently selected from the group consisting of halo, alkyl, aryl, heteroaryl, heterocyclyl, trifluoromethyl, $OR^6$, $NR^6R^7$, $SR^6$, $SO_2R^6$, CN, $SO_2N(R^6R^7)$ and $NO_2$;

$R^2$ is alkyl, cycloalkyl, alkenyl, alkynyl, trifluoromethyl, —$OR^7$, —$SR^7$, hydroxyalkyl, haloalkyl, aryl, heteroaryl, halo, CN, formyl, nitro, alkylcarbonyl, aralkylcarbonyl, heteroaralkylcarbonyl, or -alkylene-N($R^6R^9$) (where $R^8$ and $R^9$ independently represent H or alkyl, or $R^8$ and $R^9$ taken together with the nitrogen in —N($R^8R^9$) form a five- to seven- membered heterocycle);

$R^3$ is —$NR^4R^5$, 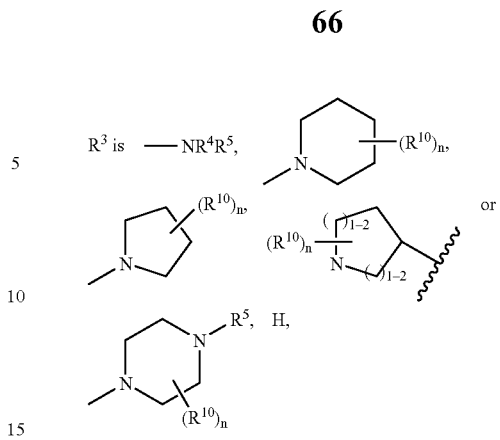

alkyl, alkylthio, aralkylthio, alkylsulfinyl, or aralkylsulfinyl;

$R^4$ is alkyl, cycloalkyl or heterocyclyl, wherein each of said alkyl, cycloalkyl and heterocyclyl can be unsubstituted or optionally independently substituted with 1–4 substituents which can be the same or different, each substituent being independently selected from the group consisting of halo, alkyl, hydroxymethyl, hydroxyethyl, hydroxypropyl, trifluoromethyl, $OR^6$, $NR^6R^7$, $SR^6$, $SO_2R^6$, CN, $SO_2N(R6R7)$ and $NO_2$;

$R^5$ is H, alkyl, aryl, heteroaryl, arylalkyl, cycloalkyl, heterocyclyl, acyl or heteroarylalkyl;

$R^6$ is H, alkyl or aryl;

$R^7$ is H or alkyl;

$R^{10}$ is halo, alkyl, hydroxyalkyl, trifluoromethyl, $OR^6$, $NR^8R^7$, $SR^6$, $SO_2R^6$, CN, $SO_2N(R^6R^7)$ or $NO_2$; and n is 0 to 4, and when n is 2–4, the n moieties can be the same or different, each being independently selected, with the following provisos:

(i) that when $R^2$ is $C_1$–$C_4$ alkyl and $R^5$ is H, then $R^4$ is not a $C_1$–$C_4$ alkyl;

(ii) that when $R^2$ is halo, CN, formyl, nitro, alkylcarbonyl, aralkylcarbonyl, heteroaralkylcarbonyl, or -alkylene-N($R^8R^9$), then: (a) $R^3$ is not H, alkylthio, aralkylthio, alkylsulfinyl, aralkylsulfinyl, or —$NR^4R^5$, and (b) n is not 0; and (iii) that when $R^2$ is alkyl, cycloalkyl, alkenyl or alkynyl, then $R^3$ is not NH(methyl), N ,N(dimethyl), NH(acetyl), N(methyl)(acetyl), H, alkyl, alkylthio, aralkylthio, alkylsulfinyl, or aralkylsulfinyl.

2. The pharmaceutical composition of claim 1, additionally comprising one or more agents selected from the group consisting of cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, 5FU, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, or Hexamethylmelamine.

3. A pharmaceutical composition comprising one or more compounds selected from:

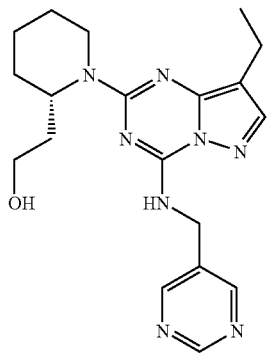

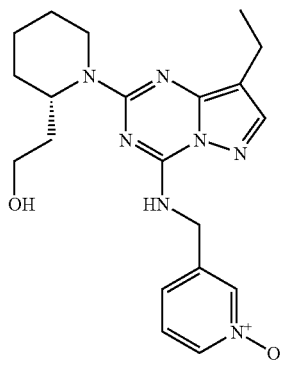

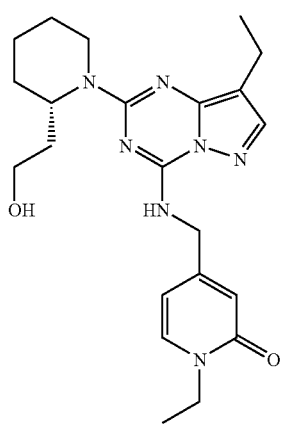

-continued

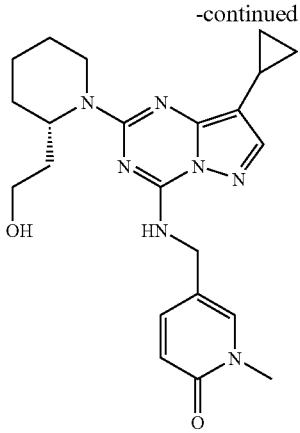

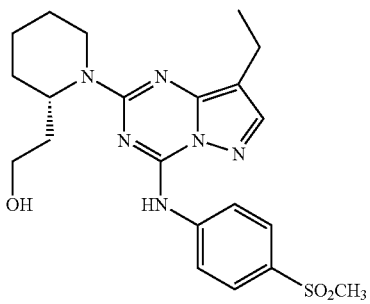

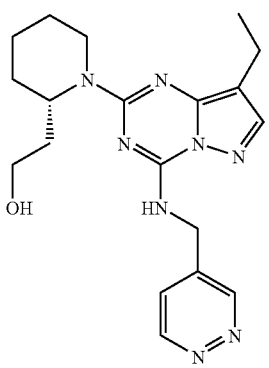

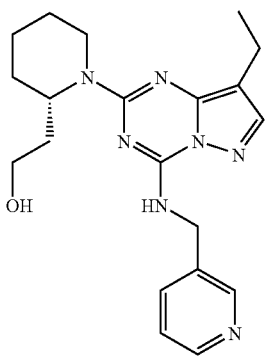

-continued

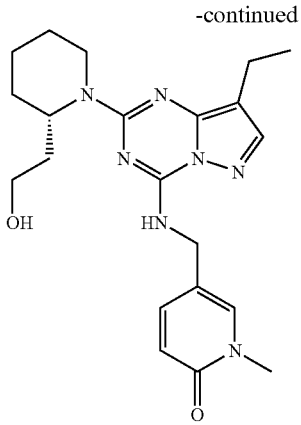

or a pharmaceutically acceptable salt, or ester thereof.

4. The pharmaceutical composition of claim 3, additionally comprising one or more agents selected from the group consisting of cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, 5FU, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil , Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, or Hexamethylmelamine.

* * * * *

UNITED STATES PATENT AND TRADEMARK OFFICE
CERTIFICATE OF CORRECTION

PATENT NO. : 7,166,602 B2  
APPLICATION NO. : 11/335383  
DATED : January 23, 2007  
INVENTOR(S) : Timothy J. Guzi and Kamil Paruch It is certified that error appears in the above-identified patent and that said Letters Patent is hereby corrected as shown below:

In the Claims:

Claim 1, col. 65, lines 63- 64:   Please correct

"–alkylene-N($R^6R^9$)" to

-- –alkylene-N($R^8R^9$) --

Claim 1, col. 66, line 31:   Please correct

"N$R^8R^7$"  to

-- N$R^6R^7$ --

Signed and Sealed this

Twenty-seventh Day of March, 2007

JON W. DUDAS  
*Director of the United States Patent and Trademark Office*